United States Patent [19]

Chromecek et al.

[11] Patent Number: 4,655,957

[45] Date of Patent: Apr. 7, 1987

[54] CONTACT LENS CLEANING COMPOSITION WITH POLYMERIC BEADS

[75] Inventors: Richard C. Chromecek, Goshen, Conn.; Lai Ogunbiyi, Fairport, N.Y.; Thomas M. Riedhammer, Rochester, N.Y.; Francis X. Smith, Walworth, N.Y.

[73] Assignee: Bausch & Lomb Incorporated, Rochester, N.Y.

[21] Appl. No.: 859,183

[22] Filed: Apr. 28, 1986

Related U.S. Application Data

[63] Continuation of Ser. No. 624,440, Jun. 25, 1984, abandoned.

[51] Int. Cl.⁴ .......................... C11O 7/26; A61K 7/00

[52] U.S. Cl. .............................. 252/174.23; 252/106; 252/163; 252/165; 252/173; 252/174.15; 252/174.17; 252/174.21; 252/542; 252/544; 252/DIG. 2; 252/DIG. 14; 134/7; 134/42

[58] Field of Search ...................... 252/174.23, 174.15, 252/174.17, 174.21, 173, 165, 106; 134/7, 42

[56] References Cited

U.S. PATENT DOCUMENTS

| | | | |
|---|---|---|---|
| 3,583,957 | 6/1971 | Chromecek et al. | 521/29 |
| 3,888,782 | 6/1975 | Boghosian et al. | 252/106 |
| 4,029,817 | 6/1977 | Blanco et al. | 424/329 |
| 4,046,706 | 9/1977 | Krezanosk | 252/106 |
| 4,071,377 | 1/1978 | Schwuger et al. | 252/99 |
| 4,493,783 | 1/1985 | Su et al. | 252/174.23 |

FOREIGN PATENT DOCUMENTS 0063472 4/1982 European Pat. Off. .

*Primary Examiner*—Paul Lieberman
*Assistant Examiner*—John F. McNully
*Attorney, Agent, or Firm*—Bernard D. Bogdon; DeWitt M. Morgan

[57] ABSTRACT

This invention relates to a cleansing composition comprising a particulate hydrophilic polymer or copolymer or mixture thereof and methods for cleaning various articles including contact lenses using the composition disclosed herein.

6 Claims, No Drawings

CONTACT LENS CLEANING COMPOSITION WITH POLYMERIC BEADS

This is a continuation of co-pending application Ser. No. 624,440 filed on June 25, 1984, now abandoned.

BACKGROUND OF THE INVENTION

1. Field of the Invention

This invention relates to the use of a particulate organic polymer in cleaning preparations.

2. Description of the Prior Art

This invention relates to the cleaning of various articles, particularly contact lenses, with a formulation containing a particulate hydrophilic polymer or copolymer or mixture thereof.

U.S. Pat. No. 4,394,179, E. J. Ellis et al., discloses the use of a silica gel abrasive in combination with a surface active agent for combined chemical and mechanical cleaning action for contact lenses.

European Patent Application No. 0 063 472 by Kai Chiang Su et al. discloses a cleaner for contact lenses which comprises a suspension containing a particulate organic polymer or polysiloxane of a hydrophobic, thermoplastic nature. The instant invention differs from Su in so far as it discloses the use of a particulate organic polymer of a hydrophilic nature which is softer and more elastic than the hydrophobic polymers taught by Su. The use of hydrophilic polymer beads in a contact lens cleaner is superior to the use of hydrophobic polymeric particles partly because the hydrophilic beads, being softer and spongier, are less likely to scratch the lens surface or to irritate the eye if left on a lens which is then placed on the eye.

SUMMARY OF THE INVENTION

In accordance with this invention, there is provided a composition for cleaning various articles, including contact lenses, the improvement comprising the inclusion of a particulate hydrophilic polymer or copolymer or mixture thereof. General purpose cleaning formulations will typically include aqueous suspensions of particulate hydrophilic polymer to which one or more apropriate surfactants are added. Typically, the composition for cleaning contact lenses will comprise an aqueous suspension having 0.001 to 25 weight percent of a particulate hydrophilic polymer in a buffered, isotonic solution containing one or more surfactants and optional preserving and sequestering agents.

DESCRIPTION OF THE PREFERRED EMBODIMENTS

More particularly, this invention relates to a composition comprising a particulate hydrophilic polymer or copolymer or mixture thereof having utility as a facial scrub or heavy-duty hand cleaner, automotive orhoushold cleaner, vinyl or leather cleaner, or contact lens cleaner and methods for using the composition disclosed herein.

Applicants have discovered that particulate hydrophilic polymers in aqueous suspension are effective cleaning agents.

Applicants have discovered, in particular, the effectiveness of suspensions of particulate hydrophilic polymers for removing debris, particularly proteinaceous deposits, from contact lenses without scratching the lens surface, thereby altering the parameters of the lens or causing eye irritation. This invention is applicable to the cleaning of hard, hard gas-permeable, and soft contact lenses but is particularly efficacious for soft contact lenses which have a greater affinity for protein deposits. The hydrophilic polymeric bead surfaces attract debris from the lens. As debris adheres to the bead surfaces, a new equilibrium is established, distributing lens debris between the bead surfaces and lens surface. This transfer of lens debris to the bead surfaces has a cleansing effect on the contact lens surface.

While not wishing to be bound by any particular theory, applicant believes that the effectiveness of particulate hydrophilic polymers in removing surface debris may be due to the physical attraction between the hydrophilic beads and the lens debris. Just as the debris is attracted to and deposited on the polymeric contact lens, the hydrophilic polyermic beads also attract deposits of lens debris. The introduction of the hydrophilic beads is believed to disrupt the equilibrium existng between the lens debris and the lens upon which it is deposited.

The particulate hydrophilic polymer is prepared by solution polymerization of selected monomers or comonomers in the presence of conventional crosslinkers, accelerators, and initiators. The preparation of the hydrophilic beads is well known, see for example U.S. Pat. No. 3,583,957 by Richard Chromecek et al. Suitable hydrophilic polymers include poly(hydroxyalkyl methacrylate), poly(hydroxyalkyl acrylate), N-vinyl lactam, or a mixture thereof. N-vinyl lactam includes (a) N-vinyl lactams per se and (b) other heterocyclic N-vinyl monomers. Illustrative of the N-vinyl lactams that are employed in this invention are: N-vinyl-2-pyrrolidinone, N-(1-methyl vinyl)pyrrolidinone, N-vinyl-2-piperidone and N-vinyl-2-caprolactam which may be substituted in the lactam ring by one or more lower alkyl groups such as methyl, ethyl or propyl, e.g., N-vinyl-5-methyl pyrrolidinone, N-vinyl-3,3-dimethyl pyrrolidinone, N-vinyl-5-ethyl pyrrolidinone and N-vinyl-6-methyl piperidone. Illustrative of the other heterocyclic N-vinyl monomers used in preparing the copolymers of this invention are: N-vinyl imidazole, N-vinylsuccinimide, N-vinyl diglycolylimide, N-vinyl glutarimide, N-vinyl-3-morpholinone and N-vinyl-5-methyl-3-morpholinone. The lactam may be an admixture of two or more lactam monomers to give hydrogels having the particularly desired characteristics. The preferred polymer for these beads is poly(hydroxyethyl methacrylate). These beads are prepared by heating a solution containing hydroxyethyl methacrylate, methyl methacrylate, and ethylene glycol dimethacrylate in the presence of tert-butyl peroctoate.

The composition of the polymeric beads can be varied by the use of a modulus modifier. A modulus modifier selected from the group of isobornyl acrylate, isobornyl methacrylate, monomethacrylate, dicyclopentadienyl acrylate, dicyclopentadienyl methacrylate adamantyl acrylate, adamantyl methacrylate, isopinocamphyl acrylate, isopinocamphyl methacrylate, menthyl methacrylate, menthyl acrylate, tertiary-butylcyclohexyl methacrylate, isopropylcyclopentylacrylate, tertiarypentylcycloheptylmethacrylate, tertiarybutylcyclohexylacrylate, isohexylcyclopentylacrylate, methylisopentyl cyclooctylacrylate, and tertiarybutylstyrene may be added to the reaction mixture to improve the modulus property of the resulting polymer or copolymer. The modifier, when employed, is generally present in an amount from 90 to 30 parts by weight per 10 to 70 parts by weight of the above described hydrophilic polymers.

The preferred particulate hydrophilic polymer is of a spherical shape resembling beads ranging in size from 0.1 to 10 microns in diameter and having an average particle size of 0.5 micron. The particulate polymer is suspended in a carrier such as water or isotonic saline solution to which one or more surfactants, preservatives, stabilizers, buffering agents, tonicity adjusters, and thickening agents may be added. The amount of polymeric bead in suspension may range from 0.001 to 25 weight percent, the preferred concentration being 5%.

Preferred nonionic surfactants for this invention include ethylene oxide/propylene oxide surfactants, for example, poloxamers and their block polymers of tetrafunctional initiators such as ethylenediamine, e.g. poloxamine 1107 (tradename Tetronic 1107) and ethoxylated lauramide (tradename Amidox C5) in concentrations ranging from 0.01% to 10% with the preferred concentration being 5%. Additional nonionic surfactants for this invention may be selected from the polyethylene glycol esters of fatty acids (e.g., coconut, polysorbate), polyoxyethylene or poloxypropylene ethers of higher alkanes ($C_{12}$–$C_{18}$). Examples of suitable nonionic surfactants include polysorbate (20) (tradename Tween 20), polyoxyethylene (23) lauryl ether (tradename Brij 35), polyoxyethylene (40) stearate (tradename Myrj 52) and polyoxyethylene (25) propylene glycol stearate (tradename Atlas G 2612). Other nonionic surfactants suitable for use in this invention can be readily ascertained, in view of the foregoing description, from McCutcheon's Detergents and Emulsifiers, North American Edition, McCutcheon Division, MC Publishing Co., Glen Rock, NJ 07452, U.S.A., 1980.

Antibacterial agents in an amount from 0.00001 to 0.5 weight percent may be added to inhibit bacterial growth in the composition. Suitable examples of such agents include thimerosal, sorbic acid, phenylmercuric salts (e.g., nitrate, borate, acetate, chloride, or gluconate), 1,5-pentanedial, the polymers and water-soluble salts of hexamethylene biguanides, and benzalkonium chloride. Cocamidopropyl betaine (tradename Lexaine C) is an example of a suitable amphoteric surfactant which functions as a preservative in this composition. For this invention, the preferred concentration of Lexaine C is 0.11%.

In addition to the active ingredients previously described, buffers, optional tonicity agents, sequestering agents, and humectants are included in contact lens cleaners. Suitable buffers include sodium or potassium citrate, citric acid, boric acid, sodium bicarbonate, sodium borate, and various mixed phosphate buffers including combinations of $Na_2HPO_4$, $NaH_2PO_4$, and $KH_2PO_4$. Generally, buffers may be used in amounts ranging from about 0.05% to 2.5% with the preferred concentration being 0.1 to 1.5%. Glycerol or propylene glycol in a preferred concentration of 15% are suitable tonicity agents. Sequestering agents such as ethylenediaminetetracetic acid (EDTA) and its disodium salts may be added in amounts ranging from 0.001 to 2.0%.

The composition is generally used by applying it to a surface, rubbing the surface with the composition, and rinsing or wiping the cleansed surface. The method of use of the cleaning preparation for contact lenses comprises having the wearer of the contact lenses remove the lenses from the eyes. The cleaning preparation is shaken to insure homogeneity and a small amount is applied to the lenses. The lenses are then rubbed with the cleaning preparation and thereafter rinsed with preserved saline solution. In an alternate cleaning method, the cleaning preparation may be applied to a pad or sponge which may be used to scrub the surface to be cleaned.

The following examples are illustrative only and should not be construed as limiting the invention. All parts and percentages referred to herein are on a weight percent basis.

Preparatory Examples

EXAMPLE I

Poly(hydroxyethyl methacrylate) beads are prepared by dissolving 4 grams of ethylene glycol dimethacrylate and 16 grams of hydroxyethyl methacrylate in 200 ml of xylene in a 2 liter round-bottom flask equipped with a reflux condenser. 0.2 ml tert-butyl peroctoate is added and the solution is stirred and heated to 80° C. +5° C.

After heating from 30 minutes to several hours, sudden polymerization with considerable exotherm occurs and a solid white polymer precipitates. Heating without stirring is continued for another 30 minutes. The reaction mixture is then cooled, diluted with xylene, and filtered. The polymer is washed with xylene and vacuum-dried. Drying can be hastened by washing the precipitate with ethyl ether or hexane.

EXAMPLE II

Following the procedures of Example I, copolymeric beads are prepared by adding 4 grams of methylmethacrylate to the reaction mixture.

EXAMPLE III

Following the procedures of Example II, copolymeric beads are prepared by substituting N-vinyl pyrrolidinone for methylmethacrylate of Example II.

The Invention

EXAMPLE IV

An aqueous facial cleaning composition is prepared having the following formulation:

| | Wt. % |
|---|---|
| Beeswax USP (white) | 13.0 |
| Sorbitan Sesquioleate | 2.0 |
| Stearyl Alcohol | 0.34 |
| Propylparaben | 0.10 |
| Petrolatum White | 26.85 |
| Methylparaben | 0.10 |
| Quaternium-15* | 0.10 |
| Perfume | qs |
| Distilled Water qs | 1 liter |
| Polymeric Beads of Example I | 10% suspension in above solution |

*Quaternium-15, listed in the CTFA Cosmetic Ingredient Directory, The Cosmetic, Toiletry, and Fragrance Association, Washington, D.C., (2nd Edition), is chloroallyl metheneamine chloride The above formulation is prepared by heating 750 ml distilled water and adding the beeswax, sorbitan sesquioleate, stearyl alcohol, propylparaben, petrolatum white, methyl paraben, Quaternium-15, and perfume. The pH is adjusted to 7.0–7.4 by the addition of 1N HCl and sufficient distilled water to make one liter is then added.

The suspension of polymeric beads in the above solution is prepared by adding 100 grams of the solution to 10 grams of the beads and mixing at high speed, such as homogenization. The suspension is covered and allowed to stand overnight at room temperature. This suspension is effective as a facial scrub.

EXAMPLE V

An aqueous hand wash is prepared having the following formulation:

| | Wt. % |
|---|---|
| Sodium Laureth-7 Sulfate | 15.0 |
| Cocamido Betaine | 8.0 |
| Lauric acid diethanolamide | 3.0 |
| Beeswax | 2.0 |
| Poystyrene Latex | 0.75 |
| Sodium Chloride | 1.50 |
| Polyethylene Glycol 6000 Distearate | 0.75 |
| Color | qs |
| Perfume | qs |
| Distilled Water qs | 1 liter |
| Polymeric beads of Example II | 8% suspension in above solution |

The above formulation is prepared by the method described in Example III.

EXAMPLE VI

An aqueous contact lens cleaning composition is prepared having the following formulation:

| | Wt. % |
|---|---|
| $Na_2HPO_4$ | 5.0 |
| $Na_2EDTA$ | 5.5 |
| Sorbic Acid | 1.1 |
| Glycerol | 15.0 |
| Cocamidopropyl Betaine | 1.1 |
| Polyvinyl Alcohol | 10.0 |
| Poloxamine 1107* | 100.0 |
| Ethoxylated alkylolamides** | 100.0 |
| Distilled Water qs | 1 liter |
| Copolymeric beads of Example III | 5% suspension in above solution |

*Flake grade, molecular weight 14,500, 70% (wt.) poly(oxyethylene)
**Amidox C5, Stepan Chemical Co.

The solution is prepared by heating 750 ml distilled water and adding the disodium hypophosphate, disodium EDTA, sorbic acid, glycerol, cocamido betaine, and polyvinyl alcohol. Once the polyvinyl alcohol is completely dissolved, heat is no longer applied to the solution. While the solution is still warm, poloxamine 1107 and Amidox C5 are added. The pH is adjusted to 7.0 by the addition of 1N HCl and the volume adjusted to one liter with distilled water.

A suspension of polymeric beads is prepared by adding 95 grams of the solution to 5 grams of the beads and mixing at high speed. The suspension is covered and allowed to stand overnight at room temperature. This suspension is effective for removing protein deposits from contact lenses.

EXAMPLE VII

An aqueous contact lens cleaning composition is prepared having the following formulation:

| | Wt. % |
|---|---|
| Poloxamine 1107 | 1.00 |
| Gelatin | 0.10 |
| Hydropropylmethycellulose | 0.59 |
| Amidox C-5 | 1.50 |
| Cocamidopropyl Betaine | 0.25 |
| Disodium Edetate | 0.11 |
| Sodium Borate | 0.15 |
| Boric Acid | 0.80 |
| Sodium Chloride | 0.30 |
| Polyhexamethylene | 1.1 ppm |
| Polymeric Beads of Example I | 5.0 |

The above formulation is prepared by the method described in Example IV. Protein and other deposits are removed from contact lenses by placing a small quantity of the composition on the lens, rubbing it between the fingers, and rinsing with saline. Inspection of the lens after this procedure demonstrates effective removal of lens debris.

EXAMPLE VIII

An aqueous contact lens cleaning composition is prepared having the following formulation:

| | Wt. % |
|---|---|
| $Na_2HPO_4$ | 5.00 |
| $Na_2EDTA$ | 5.50 |
| Sodium Chloride | 6.75 |
| Sorbic Acid | 1.10 |
| Lexaine C | 1.10 |
| Polyvinyl Alcohol | 10.00 |
| Tetronic 1107 | 100.00 |
| Amidox C5 | 100.00 |
| Distilled Water qs | 1 liter |
| Polymeric Beads of Example II | 10% suspension in above solution |

The above formulation is prepared by the method described in Example II. Protein and other deposits are removed from contact lenses by placing a small quantity of the composition on the lens, rubbing it between the fingers, and rinsing with saline. Inspection of the lens after this procedure demonstrates effective removal of lens debris.

The foregoing examples and methods have been described in the foregoing specification for the purpose of illustration and not limitation. Many other modifications and ramifications will naturally suggest themselves to those skilled in the art based on this disclosure. These are intended to be comprehended as within the scope of this invention.

The embodiments of the invention in which an exclusive property or privilege is claimed are defined as follows:

1. An aqueous suspension for cleaning deposits from contact lenses and other articles comprising one or more surfactants selected from the group consisting of nonionic or amphoteric surfactants and 0.001 to 25 weight percent of a bead shaped particulate hydrophilic cross-linked vinyl-type homopolymer or copolymer selected from the group consisting of poly(hydroxyalkyl methacrylate), poly(hydroxyalkyl acrylate), and poly N-vinyl lactam or mixtures thereof.

2. The composition of claim 1 wherein said hydrophilic polymer or copolymer comprises poly(hydroxyethyl methacrylate).

3. The composition of claim 2 comprising poly(hydroxyethyl methacrylate) beads and a poly(oxypropylene)-poly(oxyethylene) adduct of ethylene diamine having a molecular weight ranging from about 14,500 to about 19,000 wherein at least 70 weight percent of the adduct is poly(oxyethylene), in an aqueous suspension.

4. The composition of claim 1 wherein the hydrophilic polymer is a spherical bead having a particle diameter of from 0.1 to 10 microns.

5. A method for cleaning contact lenses comprising applying the composition claimed in any one of claims 1, 2–4 to a contact lens, rubbing the lens with said composition, and thereafter rinsing the lens.

6. A method for cleaning contact lenses comprising applying the composition of any one of claims 1 and 2 through 6 to a cleansing pad, rubbing the contact lens with said pad, and thereafter rinsing the lens.

* * * * *

UNITED STATES PATENT AND TRADEMARK OFFICE

CERTIFICATE OF CORRECTION

PATENT NO. : 4,655,957

DATED : April 7, 1987

INVENTOR(S) : Chromecek, Ogunbiyi, Riedhammer, and Smith

It is certified that error appears in the above-identified patent and that said Letters Patent are hereby corrected as shown below:

Claim 6, line 3, change "6" to -- 4 --.

Signed and Sealed this

Fifteenth Day of December, 1987

*Attest:*

DONALD J. QUIGG

*Attesting Officer*

*Commissioner of Patents and Trademarks*